United States Patent [19]

Tomlinson et al.

[11] Patent Number: 5,794,769
[45] Date of Patent: Aug. 18, 1998

[54] PERSONAL AND EASILY-ACCESSIBLE CARRIER FOR A CONDOM

[76] Inventors: Robert J. Tomlinson, 81 Devon La.; Cheryl M. Sinnott, 20 Devon La., both of Watsonville, Calif. 95076

[21] Appl. No.: 753,261

[22] Filed: Nov. 12, 1996

[51] Int. Cl.[6] .................................................. A45C 11/00
[52] U.S. Cl. .......................... 206/69; 383/43; 150/900; 2/312
[58] Field of Search ........................... 206/69; 383/43; 150/900; 450/150; 2/312, 247, 240

[56] References Cited

U.S. PATENT DOCUMENTS

| | | | |
|---|---|---|---|
| 1,070,250 | 8/1913 | Hamburger | 2/240 X |
| 2,040,271 | 5/1936 | Rosenzweig | 383/43 X |
| 2,227,390 | 12/1940 | Green | 383/43 X |
| 3,251,390 | 5/1966 | Evans | 383/43 X |
| 5,141,141 | 8/1992 | Leone | 2/312 X |
| 5,172,430 | 12/1992 | Lerma-Solis | 206/69 X |
| 5,460,188 | 10/1995 | Barrett, Sr. | 206/69 X |

*Primary Examiner*—Jacob K. Ackun
*Attorney, Agent, or Firm*—Donald R. Boys

[57] ABSTRACT

A condom carrier comprises a flexible loop having a liquid-impermeable pocket for carrying a condom. The pocket has an opening along one edge that may be sealed with a condom in the pocket and unsealed to remove the condom from the pocket. In some embodiments the liquid-impermeable pocket is mounted directly to the inside or the outside of the loop, and in others the loop has a primary pocket inside or outside the loop, and the liquid impermeable secondary pocket fits into the primary pocket. The liquid impermeable pocket has a user-operable seal along one edge that may be opened to insert a condom and closed to contain the condom without leakage of any liquid placed in the liquid-impermeable pocket along with the condom. The user-operable seal is a quick-release seal that may be operated to open with one hand, typically with pressure from one or two fingers.

15 Claims, 3 Drawing Sheets

PERSONAL AND EASILY-ACCESSIBLE CARRIER FOR A CONDOM

FIELD OF THE INVENTION

The present invention is in the field of personal garments and pertains in particular to easily-accessible storage apparatus for disease and birth-control equipment such as condoms.

BACKGROUND OF THE INVENTION

It is a well-documented fact that AIDS is contracted through body fluids of an infected person coming in contact with those of a non-infected person. Perhaps the most certain transmission vectors are blood contact and semen contact. The primary vector is through sexual contact/intercourse.

Public, governmental and private-industry organizations have tried to inform the general public that this nearly always fatal disease can be stopped if awareness is followed by action.

Faith in our nation's blood banks has been restored by proper donor screening. IV drug users have programs available to bring greater awareness of the dangers of sharing needles, and the general public has been informed both at an academic level as well as by media exposure, to the dangers of having unprotected sex. It has been noted however, that a large percent of even educated individuals still involve themselves in high risk unprotected sexual activity.

In preceding studies, it is also recognized that in heterosexual relationships over 86% of condom-carrying partners are female. In the male homosexual relationship, (which the CDC recognizes as a high risk group of the general population) 91% of a least one of the partners carries a condom. A recent Durex Global Survey of Sex showed that 50% of women who carry condoms, use condoms.

The perplexing question then is: Why, with all of the information available on the risks of the spread of this terrifying disease do the knowledgeable agencies still list sexual transmission as the number one cause of continuing infectious spread. What is so difficult about tearing open a package and putting on the condom?

Human nature dictates that of all our emotions, Anger, Rage, Depression, Sadness, Happiness, Elation, Determination, Drive, Desire, Lust, and finally Sex, that Sex is the strongest. It is said in many studies of the humanities that sexuality is 5% physiological, and 95% psychological. This being true, it can safely be assumed that in order to facilitate the application of a condom, it must not only fit physically but the more important issue, is it needs to fit psychologically. The present inventors believe that the application and use of a condom must be integrated as a part of the foreplay sex act in order for more people to use condoms. This tangibility issue is at the heart of the matter.

The scientific medical community recognize that mankind is driven hardest by it's need to reproduce, and to have all of the emotions, and senses available at the time of this process of sex. Sex is a powerful emotion! We have all heard the saying "in the heat of the moment". . . . This is not scientific, these are characterized by natural emote response actions of the pituitary gland. Human sexuality is a complicated, often misunderstood and sensitive subject matter. Thousands of studies, reports, papers, and documents have been published on the matter, and the one guiding issue is always pertaining to the psychology of the subject.

It is with these thoughts that the present inventors have provided a physical product integrated with emotional responses of sex and sexuality so the application of a condom is a natural part of the process of the sex act. In the prior art, a heightened sensation of sensitivity for both partners had not been taken into consideration.

Market research by the inventors has indicated that when given the right device to introduce a condom, (as a natural progression of the passion displayed between consenting adults), they would not hesitate to utilize this life-saving device. Men and women alike have agreed that any process that inhibits or intrudes on the progress of sexuality could prevent or greatly diminish either the use, or introduction of a condom. This device would overcome the tangibility issue, and actually enhance the anticipation of using a condom.

In the final analysis the conclusion is, that the condom must first get into the head, before it can go over the head.

One of the reasons given for failure to use condoms is that both of the potential partners fail to carry a condom in a manner that the condom is available against sudden need. Although a condom may be available, to find the article of clothing where it had been stored, or the billfold or purse or to retrieve it from a storage compartment (i.e.; furniture) is just too much of an interruption in the psychology, and the thoughts of safe sex are simply ignored.

Adaptations in prior art to this problem have seen various inventions patented to allow condoms to be secreted in traditional undergarments on the theory that this will make the condom accessible, however the undergarments are discarded well in advance, hence stopping to search, relinquishing the passion.

In some inventions a condom is removed from the foil pack and placed in a condom caddy pack for later use, and the same pack can be used for sanitary disposal. U.S. Pat. No. 5,005,695 to Tennefos et al. Is an example of the latter. U.S. Pat. No. 5,172,430 to Lerma-Solis is an example of the former, wherein a condom pocket is provided in a traditional undergarment.

A continuing problem with the concept of Lerma-Solis is that traditional undergarments are traditionally discarded some time before an actual sex act occurs. Then it becomes a problem to retrieve the garment to find the condom when needed. The problem with Tennefos is that, although a condom in the caddy might be more accessible than a condom in a foil pack, and the caddy provides for disposal, the problem of accessibility at the time of need is not adequately addressed.

Another problem is that in prior art systems as described herein, and in others known to the inventors, there is no integration of the condom system with the nature of the act. The condom and its use and method of provision are still seen as foreign to the mood and act, and will often be set aside for that reason.

Yet another difficulty is that a condom, when needed, must be very easily and quickly accessed, and the solutions in the prior art are inadequate in this respect as well.

What is quite clearly needed is a condom carrier device and method that allows a person to keep a condom close at hand up to and during the time of the sex act, to have the condom readily accessible without having to invade a foil pack or other container requiring some dexterity to open, while still maintaining sterility and lubrication of the condom. At the same time the condom needs to be provided in a maimer that its availability and use may be seen as an enhancement to the act of sex rather than a deterrent, and in a manner that each partner may take his/her own responsibility for his/her own comfort and safety. It is these objects that the present invention addresses.

SUMMARY OF THE INVENTION

In a preferred embodiment of the present invention a condom carrier 30 is provided comprising an elastic loop deformable circumferentially; and a liquid-impermeable pocket attached to the elastic loop. The pocket is adapted to have a user-operable, sealable opening for inserting and withdrawing a condom. The carrier in preferred embodiments has one or more of indicia, printed matter, or other decoration.

In a preferred embodiment the sealable opening has a first side and a second side, and comprises a pre-curved leaf-spring strip mounted along the width of the first side, such that with the leaf-spring strip in its not deformed state the pocket is held closed, and with the leaf-spring strip deformed in a curve opposite the pre-curved shape the pocket is held open. In some embodiments a frame is used to provide shape to the liquid impermeable pocket.

In some embodiments the loop has a primary pocket, and a secondary liquid-impermeable pocket is adapted to fit into the primary pocket. This embodiment allows for the loop to be cleaned and maintained separate from a secondary pocket, and the secondary pocket may then be made as a disposable and replaceable item for sanitary purposes.

The present invention in its several embodiments provides an easy access carrier that may be used unobtrusively without interrupting flow of activity, and which provides a condom for use readily at hand at the time of need. Such a carrier could be worn by both sexes both as an under or over garment or on any appendage or around the waist.

DESCRIPTION OF THE PREFERRED EMBODIMENTS

Figure 1A:
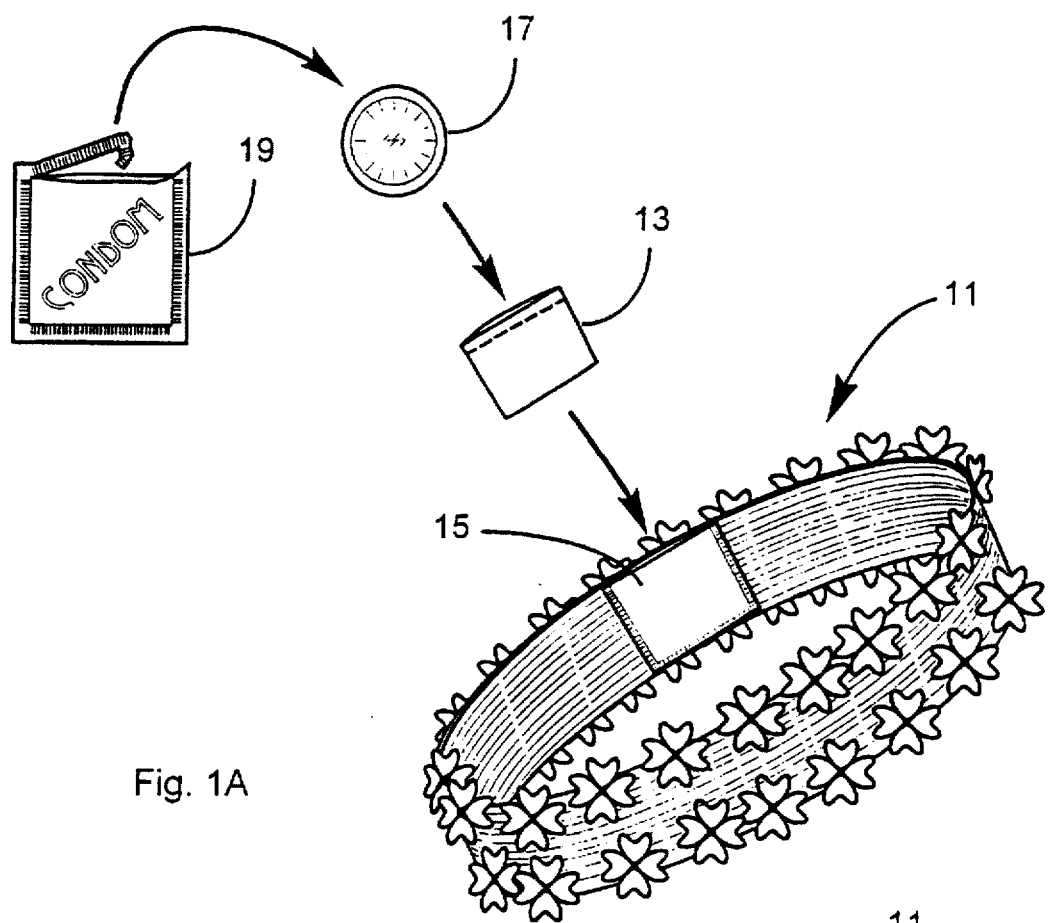
FIGS. 1A and 1B are illustration of a carrier apparatus according to an embodiment of the present invention.
Figure 1B:
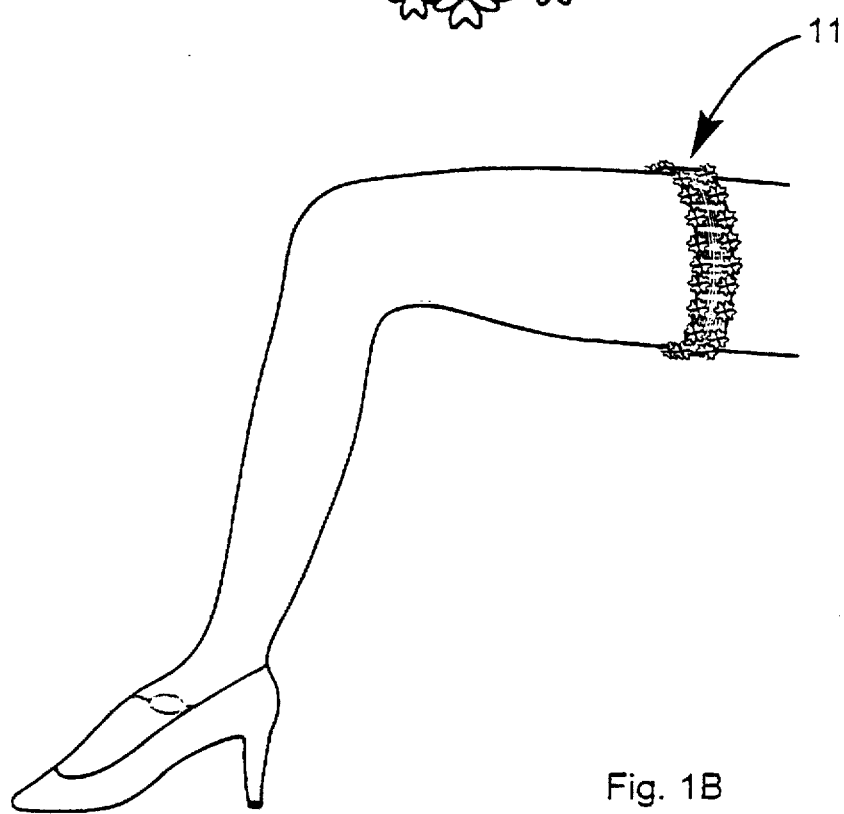

FIG. 1 is an illustration of a condom carrier apparatus according to an embodiment of the present invention, and FIG. 1B shows the device donned by a user. The carrier itself looks like a garter-like device 11 the inventors term a Loop. Loop 11 in the embodiment of FIG. 1A is elastic at least in the circumferential direction, and is composed partly of and is decorated in this embodiment with lace material to provide a seductive appearance. In other embodiments the Loop is decorated to appeal to masculine interests, and may have alternative decoration as well, or not be decorated at all. The decoration of the Loop goes to the object of providing a carrier device that would be utilized as an enhancement clothing to be integrated and recognized as a part of an individual's sexuality, therefore becoming interactive and not an interruption.

There is a primary cloth pocket 15 in this embodiment formed by adhering a patch of material to the inside of the material of the Loop as shown in FIG. 1A. Having the pocket of the Loop on the inside is preferable to allow the external decoration to extend around the circumference without interruption. In alternative embodiments the pocket could be on the outside, and there can be multiple pockets in some embodiments.

A secondary pocket 13, impervious to liquids by virtue of material of construction, such as natural or artificial latex, is provided to be placed inside primary pocket 13. Full detail of construction of secondary pocket 13 is not evident from FIG. 1A, and a full description is provided below with reference to more detailed drawings.

In practice, a user wearing a Loop according to the embodiment shown in FIG. 1A removes a condom 17 from a foil pack 19, places the condom in secondary pocket 13, and then places the secondary pocket 13 in the primary pocket 15. The user can transfer the condom just as it emerges from the foil pack, or may add other materials such as lubricants and germicides to the secondary pocket along with the condom. As described above, there may be more than one primary pocket, in which case a user might load two or more condoms in two or more secondary pockets to be placed in the primary pockets.

It is important to note that the Loop is not an undergarment that would normally be removed or discarded before or after the act of intercourse. A user may wear the Loop throughout and therefore have a condom readily available exactly at the moment of need. Also the Loop may be worn as shown on the thigh, or alternatively around another limb or even around a wearers waist, and the secondary pocket with a condom is still easily reached and incorporated without interrupting the natural flow of activity.

The Loop shown in FIGS. 1A and 1B, having a fabric primary pocket, wherein a condom is carried in a secondary pocket in the primary pocket makes it possible to have the Loop as an article of fine lingerie which may be washed and dried with the secondary pocket removed. Rather than cleaning the secondary pocket the inventors think it preferable that the secondary pocket be discarded (throwaway) after use. This, of course, is not required, and secondary pockets may be cleaned and reused.

Although the arrangement described above with reference to FIGS. 1A and 1B is considered by the inventors preferable, in another embodiment only a primary pocket is used. In this case the primary pocket is a pocket of material impervious to liquids and the rather benign chemicals expected to be used in the pocket. Such materials include natural and synthetic rubbers and some polymer materials having suitable properties. The primary pocket in this embodiment is mounted to the inside of a Loop, and in some such embodiments the Loop with its pocket is made to be a disposable item to be used once, or at most just a few times. The liquid-impermeable pocket in this case may be mounted to a Loop in a number of different ways, such as by one or more snap fasteners, by Velcro materials, by adhesives, by sewing, and so forth.

Again, as stated above, whether a secondary pocket is used or only a primary pocket, it is still necessary that the pocket be easily accessible such that a condom may be easily and unobtrusively removed without an interruption in other activity. Some special consideration of pocket closures is necessary, and these characteristics in embodiments of the invention are described below.

Figure 2A:
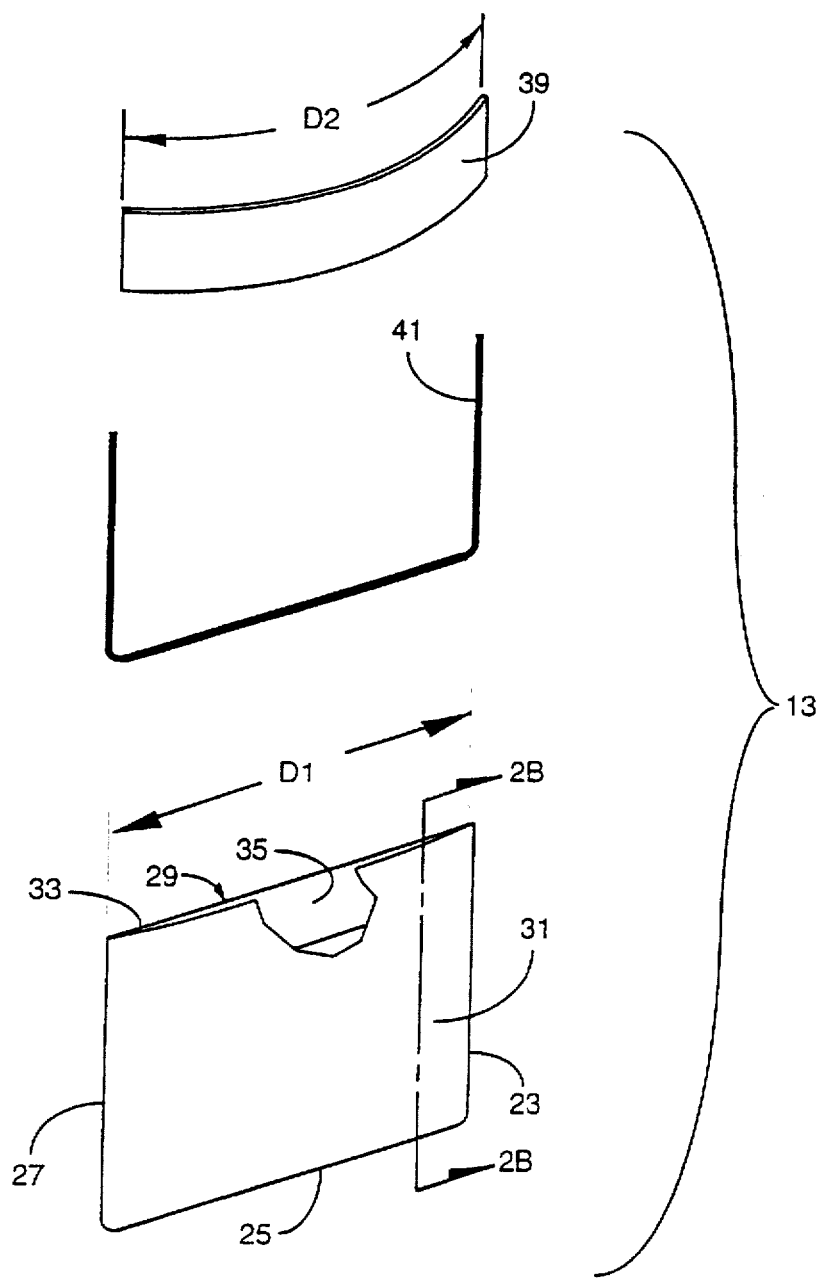
FIG. 2A is an isometric exploded view of a liquid-impervious pocket according to an embodiment of the present invention.

FIG. 2A is an exploded isometric view of a secondary pocket 13 according to a preferred embodiment of the present invention. Secondary pocket 13 is an assembly of three basic parts in this embodiment, and the parts are shown in exploded view to better describe the assembly. An envelope 21 impervious to liquids is made of natural or synthetic rubber closed on three sides 23, 25, and 27 and open on one side 29. The material is thin, on the order of such material used for surgical gloves. Envelope 21 is shown with a broken-out section to illustrate the construction of the envelope.

One side 31 of the envelope, arbitrarily called the front of the envelope in this description, comprises a single layer or sheet of the thin rubber material. The back side 33 has a folded pocket 35 along the top. As the envelope is closed (sealed) along both sides 23 and 27, pocket 35 is open only along its lower edge 37 to the interior of envelope 13.

Figure 2B:
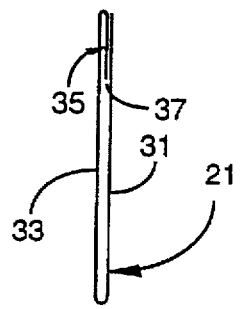
FIG. 2B is a section view of FIG. 2A taken along section line 2B—2B of FIG. 2A.

FIG. 2B is a section view taken along section line 2B—2B of FIG. 2A to better illustrate the feature of pocket 35. There are a number of different construction techniques which may be employed to accomplish the construction shown including molding, heat sealing, adhesive sealing, and the like, and the manner of construction is a matter of convenience.

Another part of secondary envelope 13 is a thin, curved plastic strip 39. This strip is preferably plastic, but could also be fashioned of one or another of several metals, and is curved in its free (unstressed) form as shown in FIG. 2A. Among the available kinds of plastic, several are suitable, such a polyvinyl chloride (PVC), Nylon, and others. An important feature of strip 39 is that it be flexible such that it may be bowed, and when bowed will exert forces to return to its passive curved form when any deformation force is released.

The third and last element of secondary pocket 13 in this embodiment is a frame 41, formed in a U-shape. In this embodiment the frame is formed from small diameter stainless steel wire, but some other material would serve. It could, for example, be made from a thin extruded plastic rod. In some embodiments no frame is used or needed. The frame is only needed in those circumstances wherein shape is seen to be needed for a pocket, and the needed shape is not provided by the material of the pocket.

In assembly, strip 39 fits into pocket 35 from inside envelope 21. The purpose of strip 39 is to provide a two-state closure for secondary pocket 13, one state open, and the other closed. The manner of operation is described more fully below.

The purpose of frame 41 is to provide at least semi-rigid structure for the assembled pocket 13, which otherwise, being constructed of very thin rubber, would be formless and shapeless. Frame 41 simply inserts into envelope against sides 23, 25, and 27. The ends of the frame are preferably inserted into 35 so the frame will be captured in the final assembly.

In practice length D2 of strip 39 measured along the surface of the strip, or end-to-end if the strip is held straight, is about 1.5 inches, and the free width D1 (unstressed or unstretched) of envelope 21 is somewhat less, say about 1.25 inches. These dimensions may vary somewhat in different embodiments. Envelope 21, including the length of pocket 35 (originally D1) must be stretched for strip 39 to be inserted into pocket 35.

Figure 2C:
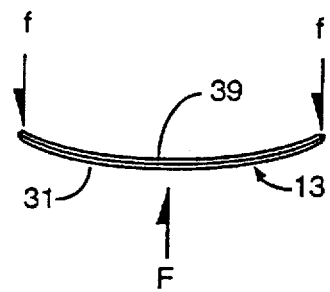
FIG. 2C is a top view of the pocket of FIG. 2A closed.

Strip 39 is inserted into pocket 35 so that the natural bow is toward the front panel 31 of envelope 21. In this circumstance, although front side 31, having been stretched, exerts a restoring force across the ends of the strip, the force is directed along the circumference of the strip, and the natural curvature of the strip is enough to keep pocket 13 closed, with the length of front side 31 at the top of the pocket pressed securely against the curved length of pocket 35. This closed state is shown from above in FIG. 2C.

Figure 2D:
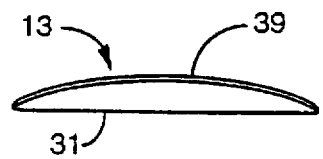
FIG. 2D is a top view of the pocket of FIG. 2A open.

If one were to grasp pocket 13 by the edges, and push on strip 39 against the direction of bowing, one may straighten the strip against the force applied by the front panel 31 and push the strip past center. That is, force F shown in FIG. 2C applied against forces f applied at the corners, if the forces are strong enough, will push the strip past center. When strip 39 is forced straight and then past center, stretched front side 31 will apply a bending force straight across the corners rather than along the circumference of the bent strip, because in this circumstance pocket 13 is free to open. That is, side 31 may remain straight and tend the shorten, causing strip 39 to bow opposite its natural bowed state. In short, the pocket snaps open. This open state of pocket 13 is shown in FIG. 2D, looking down on the pocket from the same vantage used for FIG. 2C. One may close the pocket again simply by reversing the direction of the forces on strip 39.

In the assembled form, then, pocket 13 provides a liquid-tight container which may be very quickly snapped open or closed by finger pressure, which is a very desirable characteristic for such a pocket to be used for carrying a condom in a secure and sanitary manner, while still providing ready and easy access to the condom.

Figure 2E:
FIG. 2E is top view of a flexible strip as used in some embodiments of the present invention.
Figure 2F:
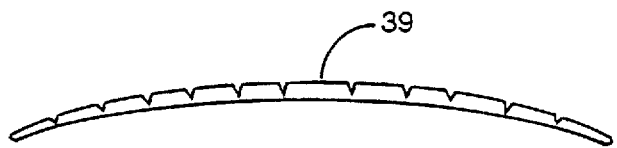
FIG. 2F is top view of an alternative flexible strip as used in some embodiments of the present invention.

The thickness and structure and material of strip 39 and the material of envelope 21, as well as the relative dimensions, determine the relative forces acting to keep the pocket closed in the one state, and the forces necessary to open the pocket to the other state. All of the variables may be adjusted by experiment to optimize the design and function of the secondary pocket. For example, in some embodiments strip 39 has a variable thickness, being thicker near the center of the strip and less thick at the ends. FIG. 2E illustrates this circumstance. This tapering affects the shape of curvature and the forces exerted. As another example, in some embodiments strip 39 has transverse grooves on one side, which causes the force necessary to bow the strip in one direction to differ considerably from the force necessary to bow the strip in the opposite direction. FIG. 2F illustrates this circumstance. The tapering and grooving may be accomplished easily by mold design for molded strips. For other manufacturing techniques and materials different processes may be used.

Referring now back to FIG. 1, one first removes a condom 17 from a foil pack such as foil pack 19, then snaps open secondary pocket 13 and inserts the condom, and optionally lubricant, spermicide, etc. into the secondary pocket. When the condom is in the secondary pocket, the user closes the secondary pocket and inserts it into primary pocket 15 on the inside of Loop 11. In this placement the secondary pocket is in its closed state, and the secondary pocket is placed in the primary pocket with the strip side (back side) of the secondary pocket toward the inside of the Loop. In this placement the back side is adjacent to a person's flesh who is wearing the Loop, and the secondary pocket may thus be opened with a firm pressure from one finger, making the condom readily accessible as needed, and in a manner that provides the least possible interruption or distraction.

In the embodiment thus far described, with the primary cloth pocket on the inside of the loop, the secondary pocket is effected by the elastic of the Loop, and the characteristics of strip 39 and the amount of pre-stretching of the secondary pocket material must be selected so that when the strip is pressed to open the secondary pocket, the action of opening will overcome the elastic of the Loop. This is considered a preferable arrangement by the inventors because the elastic of the Loop aids in keeping the secondary pocket closed. This characteristic is important because it is anticipated people will wear the Loop with a condom in the secondary pocket typically for several hours. It is intended that the closure be secure enough that users may have confidence to allow them to don a Loop when dressing for an evening out, for example, without fear that the secondary pocket may accidentally open and cause embarrassment.

In some embodiments the Loop is designed to have the primary pocket added outside the elastic of the Loop, and with the decoration (if any) of the Loop continued over the pocket. In this embodiment the elastic of the Loop is not a variable in the closure or the process of opening the secondary pocket to access a condom.

It will be apparent to those with skill in the art that there are many changes that may be made in the embodiments described above without departing from the spirit and scope of the invention. For example, although a decorated Loop has been described with lace decoration, use has been illustrated as worn by a woman, and heterosexual circumstances have been described, Loops could be decorated in many different ways attractive to males and females of any sexual persuasion, or not decorated at all. Loops may also be worn by anyone, and may be worn concealed, as a garter under other clothing, or may be worn overtly, such as an armband, with or without decoration or other indicia. Other indicia may include logos, printed matter and the like, as well as decoration with metals, jewels, and the like.

Several construction techniques have been illustrated above. Many others will occur to those with skill in the art. There are, for example, a number of ways a flexible strip may be added to a secondary pocket to provide closure and opening action according to the descriptions of embodiments of the invention. Such construction details may molded in one-piece construction for example. Strips may also be added to other material by heat adhesion, glue, fasteners, and by yet other methods.

Other details may vary as well, such as details of frames for shaping pockets. In some embodiments no such frame is needed, and the structure of a condom within a pocket provides all of the structure necessary for a pocket. In addition, sizes may vary widely in alternative embodiments, as well as materials and details of geometry of materials. There are many other details in embodiments described which may be altered without departing from the spirit and scope of the invention.

What is claimed is:

1. A condom carrier comprising:

a dedicated elastic loop deformable circumferentially; and a liquid-impermeable pocket attached to the elastic loop, the liquid-impermeable pocket having a sealable opening with a first side and a second side, including a pre-curved leaf-spring strip mounted along the width of the first side, such that with the leaf-spring strip in its not-deformed state the pocket is held closed, and with the leaf-spring strip deformed in a curve opposite the pre-curved shape the pocket is held open.

2. The condom carrier of claim 1 further comprising one or more of decoration, indicia, and printed matter on the elastic loop.

3. The condom carrier of claim 1 wherein the liquid-impermeable pocket is attached to the inside of the elastic loop.

4. The condom carrier of claim 1 wherein the liquid-impermeable pocket is attached to the outside of the elastic loop.

5. The condom carrier of claim 1 further comprising a frame adapted to fit inside the pocket, providing shape to the pocket.

6. The condom carrier of claim 5 wherein the frame is a wire formed into a U-shape.

7. A condom carrier comprising:

a dedicated elastic loop deformable circumferentially;

a primary pocket attached to the elastic loop; and a liquid-impermeable secondary pocket adapted to be carried in the primary pocket, the liquid-impermeable secondary pocket having a sealable opening with a first side and a second side, and including a pre-curved leaf-spring strip mounted along the width of the first side, such that with the leaf-spring strip in its not-deformed state the pocket is held closed, and with the leaf-spring strip deformed in a curve opposite the pre-curved shape the pocket is held open.

8. The condom carrier of claim 7 further comprising one or more of decoration, indicia, and printed matter on the elastic loop.

9. The condom carrier of claim 7 wherein the primary pocket is attached to the inside of the elastic loop.

10. The condom carrier of claim 7 wherein the primary pocket is attached to the outside of the elastic loop.

11. The condom carrier of claim 7 wherein the secondary pocket is positioned in the primary pocket with the first side toward the inside of the loop. Such that the pre-curved shape of the leaf-spring strip is curved in the same direction as the loop.

12. The condom carrier of claim 7 further comprising a frame adapted to fit inside the pocket, providing shape to the pocket.

13. The condom carrier of claim 12 wherein the frame is a wire formed into a U-shape.

14. A carrier pocket comprising:

an envelope of elastically-extensible material permanently sealed on three edges; and a reusable, sealable opening along a fourth edge, the sealable opening having a first side and a second side of equal unextended lengths, and a laterally-flexible, pre-curved leaf-spring strip of a fixed length along the curvature greater than the unextended length, the strip mounted along the first side of the opening with the outside of the curvature facing the second side of the opening by first stretching the opening to an extended length equal to the fixed length of the leaf-spring strip;

wherein, with the strip in its normal curved state the pocket is held closed, and by deforming the strip past straight to provide a curvature opposite the normal curvature, the second side provides a force holding the pocket open.

15. The carrier pocket of claim 14 wherein the flexible material is selected from the group of materials including natural and synthetic rubber.

* * * * *